United States Patent
Yamada et al.

[11] Patent Number: 5,976,350
[45] Date of Patent: Nov. 2, 1999

[54] METHOD OF AND APPARATUS FOR DETECTING AN ACTIVATED CONDITION OF A WIDE RANGE AIR-FUEL RATIO SENSOR

[75] Inventors: Tessho Yamada, Nagoya; Takeshi Kawai, Aichi; Yuji Oi, Nagoya; Shigeki Mori, Gifu; Satoshi Teramoto, Aichi; Toshiya Matsuoka, Gifu, all of Japan

[73] Assignee: NGK Spark Plug Co., Ltd., Nagoya, Japan

[21] Appl. No.: 08/920,722

[22] Filed: Aug. 29, 1997

[30] Foreign Application Priority Data

Aug. 29, 1996 [JP] Japan ................................. 8-247074

[51] Int. Cl.⁶ ............................................. G01N 27/407
[52] U.S. Cl. .................... 205/784.5; 204/401; 204/402; 204/425; 204/426; 205/775
[58] Field of Search .................... 204/401, 402, 204/421–429; 205/783.5, 784, 784.5, 785, 775

[56] References Cited

U.S. PATENT DOCUMENTS

| | | | |
|---|---|---|---|
| 4,626,338 | 12/1986 | Kondo et al. .......................... 204/425 |
| 5,172,677 | 12/1992 | Suzuki .................................... 123/688 |
| 5,174,885 | 12/1992 | Hayakawa et al. ..................... 204/425 |
| 5,194,135 | 3/1993 | Hayakawa et al. ..................... 204/425 |
| 5,611,909 | 3/1997 | Studer .................................... 204/401 |

*Primary Examiner*—T. Tung
*Attorney, Agent, or Firm*—Foley & Lardner

[57] ABSTRACT

A method of detecting an activated condition of a wide range air-fuel ratio sensor is provided. With this method, application of a current to a heater is started idiately after an engine is started (S00). Then, a current Icp for pumping is passed through an electromotive force cell (S10). A lapse of a predetermined time Tin is waited for (S18). After a lapse of time Tin, a voltage Vs across both electrodes of the electromotive force cell is detected (S20) and labeled as Vs0 (S22). Then, application of Icp is suspended (S30) and a routine is held on standby until a time of 25 ms elapses (S35). At the point of time when the time of 25 ms has elapsed, the voltage across the electrodes on the opposite sides of the electromotive force cell is detected (S40) and labeled as Vs1 (S45). A resistance value Rs1 is calculated from Vs0, Vs1 and Icp (S50). The resistance value Rs1 is compared with a value Rss which has been prepared previously (S55) and it is judged, when Rs1 is smaller than Rss, that the electromotive force cell has been put into an activated condition. An apparatus for detecting an activated condition of a wide range air-fuel ratio sensor is also provided.

4 Claims, 8 Drawing Sheets

FIG.7

| Vs DETECTING TIME T1 (ms) | TIME T2 (s) FOR ACTIVATION | EXHAUST GAS AIR-FUEL RATIO ($\lambda$) | DURABILITY TEST (TIMES) |
|---|---|---|---|
| 1 | 7 | 1.01 | 10254 |
| 2 | 8 | 1.008 | 11200 |
| 5 | 8.5 | 1.005 | 13050 |
| 8 | 9 | 1.002 | 17823 |
| 10 | 11 | 1.001 | 25411 |
| 20 | 11 | 1.001 | 27502 |
| 40 | 11 | 1.000 | 28305 |
| 50 | 12 | 1.000 | 29003 |
| 60 | 15 | 0.999 | 29503 |
| 80 | 17 | 0.999 | 30120 |
| 100 | 19 | 0.999 | 30221 |
| 200 | 25 | 0.999 | 30511 |

METHOD OF AND APPARATUS FOR DETECTING AN ACTIVATED CONDITION OF A WIDE RANGE AIR-FUEL RATIO SENSOR

BACKGROUND OF THE INVENTION

1. Field of the Invention

The present invention relates to a method of and apparatus for detecting whether a wide range air-fuel ratio sensor has been activated or not.

2. Description of the Related Art

For controlling an air-fuel ratio mixture to be supplied to an engine in a way as to allow the air-fuel ratio to be maintained at a target value (i.e., stoichiometric) and thereby reducing the concentration of CO, NOx and HC in the engine exhaust gases, it is known to carry out a feedback control of a quantity of fuel to be supplied to the engine. For such feed-back control, a λ (lambda) sensor whose output changes abruptly or sharply (i.e., stepwise) in response to a particular oxygen concentration, i.e., a theoretical air-fuel ratio mixture and a wide range oxygen sensor or air-fuel ratio sensor, whose output changes smoothly and continuously (i.e., not stepwise) in response to a variation of the air-fuel ratio from a lean mixture mode or range to a rich mixture mode or range are mainly used. The wide range air-fuel ratio sensor is, as mentioned above, capable of detecting the oxygen concentration in an engine exhaust gas continuously and improving the feedback control accuracy and speed, and is thus used in case the higher-speed and more accurate feedback control is required.

The wide range air-fuel sensor is provided with two cells made of oxygen ion conductive solid electrolytic bodies, which are disposed so as to oppose to each other with a certain interval or gap (measurement chamber) therebetween. One of the cells is used as a pump cell for pumping out the oxygen from or into the gap between the cells. The other of the cells is used as an electromotive force cell for generating a voltage depending upon a difference in the oxygen concentration between an oxygen reference chamber and the above gap. The pump cell is operated in such a manner that the output of the electromotive force cell is constant, and the current supplied to the pump cell to this end is measured for use as a value proportional to a measured oxygen concentration. An example of such a wide range air-fuel ratio sensor is disclosed in U.S. Pat. Nos. 5,174,885 and 5,194,135.

The above described feedback control for reducing the noxious components contained in the exhaust gases starts after warm-up of the engine is completed. This is because the wide range air-fuel ratio sensor is not active or operable until it is heated up to a predetermined temperature to make higher the activity of its oxygen ion conductive solid electrolyte. For this reason, a heater is provided to the wide range air-fuel ratio sensor in order to make it operable as soon as possible after starting of the engine.

In this connection, before the feedback control by means of the above described wide range air-fuel ratio sensor starts, the air fuel ratio is regulated to a rich mode so that the exhaust gases with a relatively high concentration of CO and HC are emitted. In order to finish the emission of such exhaust gases with a high concentration of the noxious components within a short time, judgment on whether the wide range air-fuel ratio sensor has been activated or not is made by applying a predetermined current or voltage to the electromotive force cell for measurement of the resistance in order that the wide range air-fuel ratio sensor can be put into action as early as possible after starting of engine.

Referring to FIG. 8A, a prior art technology on such judgment will be described. FIG. 8A is a graph of a voltage across an electromotive force cell, resulting when a constant current is passed through the electromotive force cell, as a function of a time elapsing after heating of the electromotive force cell starts. The electromotive force cell decreases in resistance gradually as it is heated for a longer time. That is, the temperature of the electromotive force cell is assumed on the basis of the resistance, and judgment on whether the electromotive force cell has reached a predetermined temperature at which the electromotive force cell becomes active or operable is made on the basis of the assumed temperature. In this instance, when the voltage of the electromotive force cell has reached a value Vs1, it is judged that the electromotive force cell (i.e., wide range air-fuel ratio sensor) has reached a temperature at which it becomes active, and after a margin of about 10 seconds elapses the operation of the wide range air-fuel ratio sensor is made to start.

In this connection, the reason why the wide range air-fuel ratio sensor is made to operate after a margin of about 10 seconds elapses in the above described prior art technology is that the voltage Vs of the electromotive force cell varies depending upon a variation of the surrounding atmosphere. That is, an electric potential is generated in the electromotive force cell on the basis of an oxygen concentration in the surrounding atmosphere, so the temperature that the electromotive force cell has at the time of its voltage having reached the above described value Vs1 varies depending upon whether the surrounding atmosphere shows a rich mixture or a lean mixture. For this reason, assuming that the electromotive force cell does not yet become actually active or operable even when its voltage has reached the above described Vs1, heating is continued for further 10 seconds or so.

A further accurate technology of detecting whether the electromotive force cell has become active or operable is disclosed in Japanese patent provisional publication No. 4-313056. By this technology, as shown in FIG. 8B, application of a current to the electromotive force cell is periodically stopped or suspended, whereby the resistance of the electromotive force cell is measured on the basis of the voltage fall Vsd3 resulting when the application of current to the electromotive force cell is stopped or suspended, and judgment on whether the electromotive force cell has become active or operable is made based on the resistance measured as above. That is, the voltage Vs of the electromotive force cell is the sumn of the result obtained by multiplying the resistance of the electromotive force cell and the current passed through the same, and the internal electromotive force (hereinafter also referred to simply as electromotive force) of the electromotive force cell, so the voltage fall at the time of stoppage or suspension of the supply of current to the electromotive force cell is dependent only on the resistance value of the electromotive force cell. Thus, the temperature of the electromotive force cell can be measured irrespective of the internal electromotive force which varies depending upon a variation of the surrounding atmosphere.

However, it was found that the above described prior art technology was insufficient in accuracy in detecting the resistance of the electromotive force cell. That is, the voltage across the electrodes at the opposite side surfaces of the electromotive force cell after the current or voltage to be applied to the electromotive force cell is suspended or stopped, is not necessarily constant but varies momentarily even during a quite short time (e.g., 1 ms or less), so the prior art of FIG. 8A-8B encounters such a problem that it is unclear that at what time after application of the current or voltage is suspended or stopped, measurement of the voltage across the electrodes at the opposite side surfaces of the electromotive force cell should be made for accurate detection of the activity of the sensor.

The cause of voltage variation within a quite short time has not yet been clearly explained but may roughly be assumed as follows.

As shown in FIG. 1, an electromotive force cell 24 has such a structure as having electrodes 22 and 28 at opposite side surfaces of a solid electrolytic body and is not a simple, pure resistance in view of an equivalent circuit but has characteristics of complex impedance resulting from a combination of a resistance and a latent electrostatic capacity. Accordingly, as described above, a response to a sudden, step-like variation of applied voltage (stoppage of application of voltage) does not occur in a sudden, step-like manner but exhibits a complex variation resulting from a combination of several exponential variations.

In this instance, if judgment on the activity is made by using a voltage detected at a suitable timing, there may possibly be caused a problem that the output of the wide range air-fuel ratio sensor is inaccurate or judgment on the activity is delayed with the result that the wide range air-fuel ratio cannot function properly or desirably.

SUMMARY OF THE PRESENT INVENTION

According to a first aspect of the present invention, there is proposed a method of detecting an activated condition of a wide range air-fuel ratio sensor. The air-fuel ratio sensor includes two cells each having an oxygen ion conductive solid electrolytic body heated by a heater and two porous electrodes disposed on opposite sides of the oxygen ion conductive solid electrolytic body, respectively. The two cells are disposed so as to oppose each other with a gap therebetween. One of the cells is used as a pump cell for pumping oxygen out of or into the gap, and the other of the cells is used as an electromotive force cell for generating a voltage according to a difference in oxygen concentration between an oxygen reference chamber and the gap. The method comprises a first step of applying a current or voltage to the electromotive force cell, a second step of detecting a voltage V0 across the electrodes at the opposite sides of the electromotive force cell, a third step of suspending the applying of the current or voltage to the electromotive force cell, a fourth step of detecting a voltage V1 across the electrodes at the opposite sides of the electromotive force cell after a lapse of time ranging from 10 ms to 50 ms after the third step, and a fifth step of detecting the activated condition of the air-fuel ratio sensor based on the voltage V0 detected at the second step and the voltage V1 detected at the fourth step.

In this aspect, the voltage across the electrodes on the opposite sides of the electromotive force cell, which is measured after a lapse of time ranging from 10 ms to 50 ms after application of a current or voltage to the electromotive force cell is suspended, is used for the detection, so the activated condition of the wide range air-fuel ration sensor can be detected accurately. That is, the electromotive force cell has such a structure as having the electrodes on the opposite sides of a solid electrolytic body and is not a simple, pure resistance in view of an equivalent circuit but has characteristics of complex impedance resulting from a combination of a resistance and a latent electrostatic capacity. For this reason, the voltage of the electromotive force cell after suspension of the application has a tendency to reduce gradually. In this instance, the voltage of the electromotive force cell which is measured within 10 ms immediately after suspension of the application of the current or voltage to the electromotive force cell is largely influenced by the bulk resistance of the solid electrolytic body among the resistance of the complex impedance of the electromotive force cell. In such a case, on the basis of V0 which is a voltage measured before the above described suspension of application and a voltage measured after the above described suspension of application, the activity of the bulk part of the solid electrolytic body can be detected. However, the activity of the electromotive force cell depends on not only the activity of the bulk part of the solid electrolytic body but the contact or joining condition of the electrodes to the solid electrolytic body and the activity of the electrodes of themselves, so the actual activated condition of the electromotive force cell cannot be detected unless all of the above described activated conditions are detected. On the other hand, the voltage detected after a lapse of time ranging from 10 ms to 50 ms after the above suspension of application reflects on the resistance value indicative of, among the resistance value of the complex impedance of the solid electrolytic body, not only the activated condition of the bulk part of the solid electrolytic body but all the conditions including the contact condition of the electrodes and the activated condition of the electrodes of themselves, so it becomes possible to detect the activated condition of the electromotive force cell, i.e., the activated condition of the sensor accurately. In the meantime, "supply of current from the outside for forced flow" is regarded as a similar action to application of a voltage and herein referred to "application of a current or to apply current" only for the convenience of understanding.

According to a second aspect of the present invention, in the above described method, the fifth step comprises detecting a resistance value Rs1 of the electromotive force cell on the basis of the voltage V0 and the voltage V1 and judging that the wide range air-fuel ratio sensor has been activated when the resistance value Rs1 is equal to or smaller than a predetermined value.

With this aspect, there is provided one method of detecting the activated condition of the electromotive force cell on the basis of the above described V0 and V1, wherein the activated condition is not simply detected by using V0 and V1 but these values are actually used for detecting the resistance value of the electromotive force cell and thereby detecting the activated condition of the electromotive force cell, so a parameter for detection can be one and therefore the detecting process onward can be easier.

According to a third aspect of the present invention, in the method of the first or second aspect, the third step is executed after the lapse of a predetermined time after energizing of the heater starts.

According to a fourth aspect of the present invention, in the method of the first or second aspect, the third step is executed after the voltage V0 detected at the second step becomes equal to or smaller than a predetermined value.

According to a fifth aspect of the present invention, there is provided an apparatus for detecting an activated condition of a wide range air-fuel ratio sensor, the air-fuel ratio sensor including two cells each having an oxygen ion conductive solid electrolytic body and two porous electrodes disposed on opposite sides of the oxygen ion conductive solid electrolytic body, respectively, the two cells being disposed so as to oppose each other with a gap therebetween, one of the cells being used as a pump cell for pumping oxygen out of or into the gap, the other of the cells being used as an electromotive force cell for generating a voltage according to a difference in oxygen concentration between a oxygen reference chamber and the gap, the apparatus comprising current or voltage applying means for applying a current or voltage to the electromotive force cell, V0 voltage detecting means for detecting a voltage V0 across the electrodes on the opposite sides of the electromotive force cell, suspending means for suspending the applying of the current or voltage to the electromotive force cell, V1 voltage detecting means for detecting a voltage V1 across the electrodes on the opposite sides of the electromotive force cell after a lapse of time ranging from 10 ms to 50 ms after the applying of the current or voltage to the electromotive force cell is suspended, and activity detecting means for detecting a resistance value Rs1 of the electromotive force cell on the basis of the voltage V0 and the voltage V1 and judging, when the resistance value Rs1 is equal to or smaller than a predetermined value, that the wide range air-fuel ratio sensor has been activated.

According to a sixth aspect of the present invention, there is provide an apparatus for detecting an activated condition of a wide range air-fuel ratio sensor, the air-fuel ratio sensor including two cells each having an oxygen ion conductive solid electrolytic body and two porous electrodes disposed on opposite sides of the oxygen ion conductive solid electrolytic body, respectively, the two cells being disposed so as to oppose each other with a gap therebetween, one of the cells being used as a pump cell for pumping oxygen out of or into the gap, the other of the cells being used as an electromotive force cell for generating a voltage according to a difference in oxygen concentration between a oxygen reference chamber and the gap, the apparatus comprising current or voltage applying means for applying a current or voltage to the electromotive force cell, V0 voltage detecting means for detecting a voltage V0 across the electrodes on the opposite sides of the electromotive force cell, suspending means for suspending the applying of the current or voltage to the electromotive force cell when the voltage V0 becomes equal to or smaller than a predetermined value, V1 voltage detecting means for detecting a voltage V1 across the electrodes on the opposite sides of the electromotive force cell after a lapse of tire ranging from 10 ms to 50 ms after the applying of the current or voltage to the electromotive force cell is suspended, and activity detecting means for detecting a resistance value RS1 of the electromotive force cell on the basis of the voltage V0 and the voltage V1 and judging, when the resistance value Rs1 is equal to or smaller than a predetermined value, that the wide range air-fuel ratio sensor has been activated.

In the third and fifth aspects, the suspension of application is started after a lapse of a predetermined time after energizing of the heater starts, so complicated detecting work for detecting the activated condition of the electromotive force cell which is apparently assumed to be in an inactivated condition is never done or is not uselessly repeated In the fourth and sixth aspects, in case the suspension of application starts after energizing of the heater starts as in the third aspect, detection of the activated condition may possibly be made to start with an unnecessary delay when the engine is stopped temporarily, i.e., when energizing of the heater is suspended and made to start immediately thereafter. When the voltage across the electrodes on the opposite sides of the electromotive force cell is detected under a condition of a current being kept flowing through the electromotive force cell, a rough estimation regarding the activated condition can be obtained on the basis of the measured value, so such an unnecessary delay with which detection of the activated condition is made to start can be avoided by starting the suspension of application after the voltage across the electrodes on the opposite sides of the electromotive force cell becomes equal to or smaller than a predetermined value.

The above method and apparatus are effective for solving the above noted problems inherent in the prior art method and apparatus.

It is accordingly an object of the present invention to provide a method of detecting an activated condition of a wide range air-fuel ratio sensor which can detect an activated condition of a wide range air-fuel ratio sensor accurately irrespective of a variation of a voltage applied to an electromotive force cell after application of a current to same is suspended.

It is another aspect of the present invention to provide an apparatus for carrying out the above described method of detecting an activated condition of a wide range air-fuel ratio sensor.

BRIEF DESCRIPTION OF THE DRAWINGS

FIG. 7 is a table for comparison of the durable number of times by which the sensor can be used in a test for the durability;

DETAILED DESCRIPTION OF THE PREFERRED EMBODIMENTS

Figure 1:
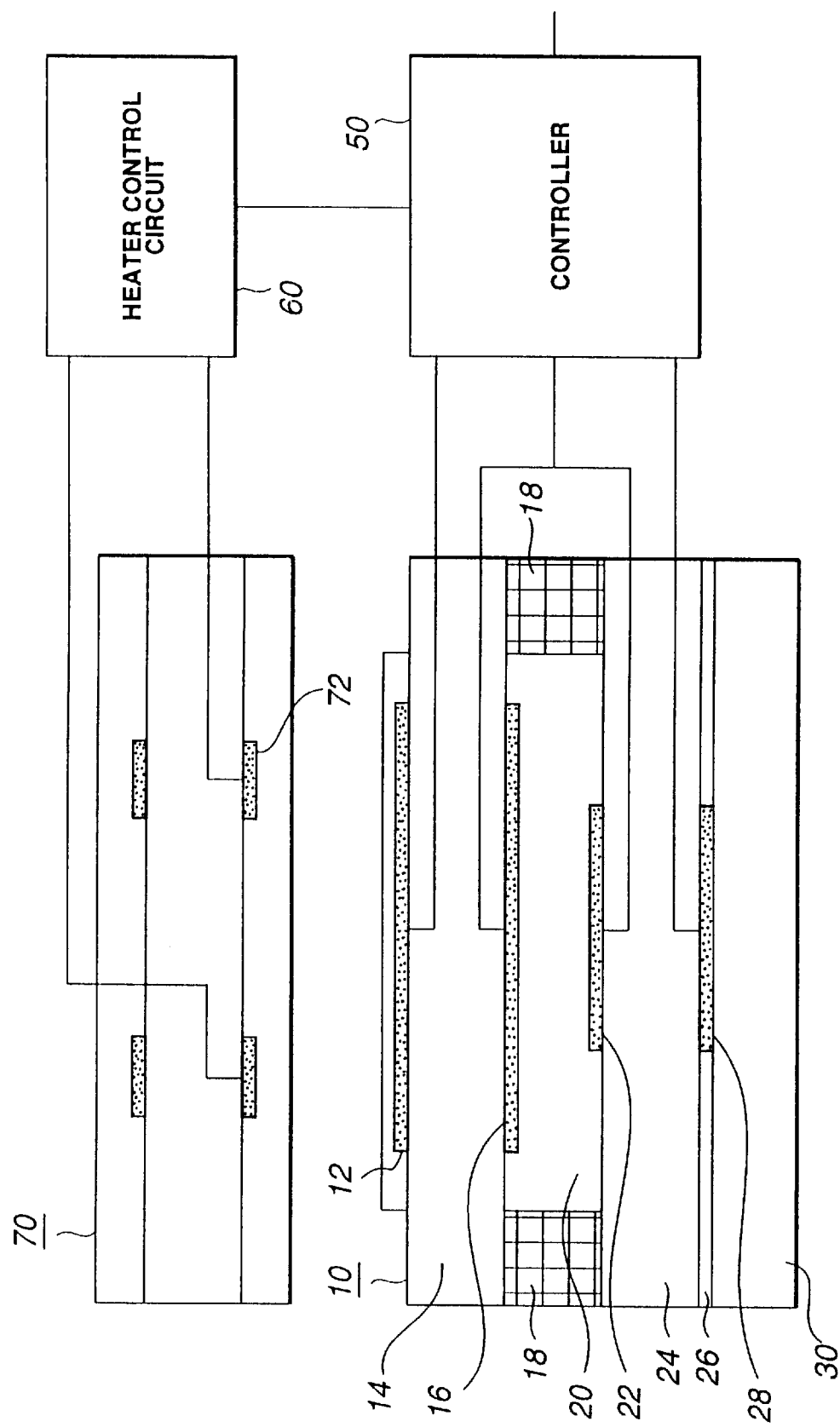
FIG. 1 is an illustration of a wide range air-fuel ratio sensor, heater control circuit and controller according to an embodiment of the present invention.

Referring first to FIG. 1, a wide range air-fuel ratio sensor according to an embodiment of the present invention is shown as including a cell unit 10 which is disposed in an exhaust system (not shown). The cell unit 10 measures the oxygen concentration in the exhaust gases and is connected to a controller 50 for measuring the temperature of the cell unit 10. To the cell unit 10, a heater 70 which is controlled by a heater control circuit 60 is attached by way of an adhesive made of ceramic. The heater 70 is made of an insulation material, i.e., a ceramic material such as alumina and has disposed therewithin a heater circuit or wiring 72. The heater control circuit 60 applies an electric power to the heater 70 in such a way that the resistance of the cell unit 10 to be measured by the controller 50 is maintained constant, whereby to maintain the temperature of cell unit 10 constant.

The cell unit 10 includes a pump cell 14, a porous diffusion layer 18, an electromotive force cell 24 and a reinforcement plate 30 which are placed one upon another. The pump cell 14 is made of solid electrolyte having an oxygen ion conductivity, i.e., stabilized or partially stabilized zirconia ($ZrO_2$) and has on the front and rear surfaces thereof porous electrodes 12 and 16 mainly made of platinum, respectively. To the front surface side porous electrode 12 which is exposed to the measured gas, a voltage Ip+ is applied for electric current Ip+ to flow therethrough, so the front surface side porous electrode 12 is referred to as an Ip+ electrode. On the other hand, to the rear surface side porous electrode 14, a voltage Ip– is applied for electric current Ip– to flow therethrough, so the rear surface side porous electrode 14 is referred to as an Ip– electrode.

The electromotive force cell 24 is similarly made of stabilized or partially stabilized zirconia ($ZrO_2$) and has on the front and rear surfaces thereof porous electrodes 22 and 28 mainly made of platinum, respectively. At the porous electrode 22 disposed on a gap (measurement chamber) 20 side, a voltage Vs– is generated by the electromotive force Vs of the electromotive cell 24, so the porous electrode 22 is referred to as a Vs– electrode. On the other hand, at the porous electrode 28 disposed on an oxygen reference chamber 26 side, a voltage Vs+ is generated, so the porous electrode 28 is referred to as a Vs+ electrode. In the meantime, the reference oxygen within the oxygen reference chamber 26 is formed or produced by pumping predetermined oxygen into the porous electrode 28. Between the pump cell 14 and the electromotive force cell 24, the gap (measuring chamber) 20 which is surrounded by the porous diffusion layer 18 is formed. That is, the gap 20 is communicated with the measuring gas atmosphere by way of the porous diffusion layer 18. In the meantime, in this embodiment, the porous diffusion layer 18 formed by filling a porous material in a predetermined place is used but in place thereof pores may be disposed in place.

By this, oxygen according to the difference in the oxygen concentration between the gas to be measured and the gas within the gap 20 is diffused into the gap 20 side by way of the porous diffusion layer 18. In this connection, when the atmosphere within the gap 20 is maintained at a theoretical air-fuel ratio, an electric potential is generated between the gap 20 and the oxygen reference chamber 26 which is maintained constant in oxygen concentration, i.e., a potential of about 0.45 V is generated between the Vs+ electrode 28 and the Vs– electrode 22 of the electromotive force cell 24. In this instance, the controller 50 regulates the current Ip flowing through the pump cell 14 in such a way that the electromotive force Vs of the above described electromotive force cell 24 is 0.45 V, whereby to maintain the atmosphere in the gap 20 at a theoretical air-fuel ratio and measure the oxygen concentration in the gas to be measured, on the basis of the pump cell current Ip for attaining such a theoretical air-fuel ratio.

Referring to FIGS. 2 to 5, actions of the controller 50 for detecting the activated condition of the wide range air-fuel ratio sensor will be described.

The controller 50 supplies, after the engine starts, a current to the heater 70 by way of the heater control circuit 60 to heat the cell unit 10 and thereby make it activated. An electric current Icp is passed through the electromotive force cell 24 to pump oxygen into the oxygen reference chamber 26 while at the same time detection on whether the electromotive force cell 24 is heated up to a higher temperature and put into an activated condition is made, on the basis of the voltage of the electromotive force cell 24, and then measurement of the concentration of oxygen is made to start. Thereafter, the current Ipc is passed through the pump cell 14 to control the atmosphere in the gap 20 in a way that the air-fuel ratio of the atmosphere is maintained theoretical.

Figure 2:
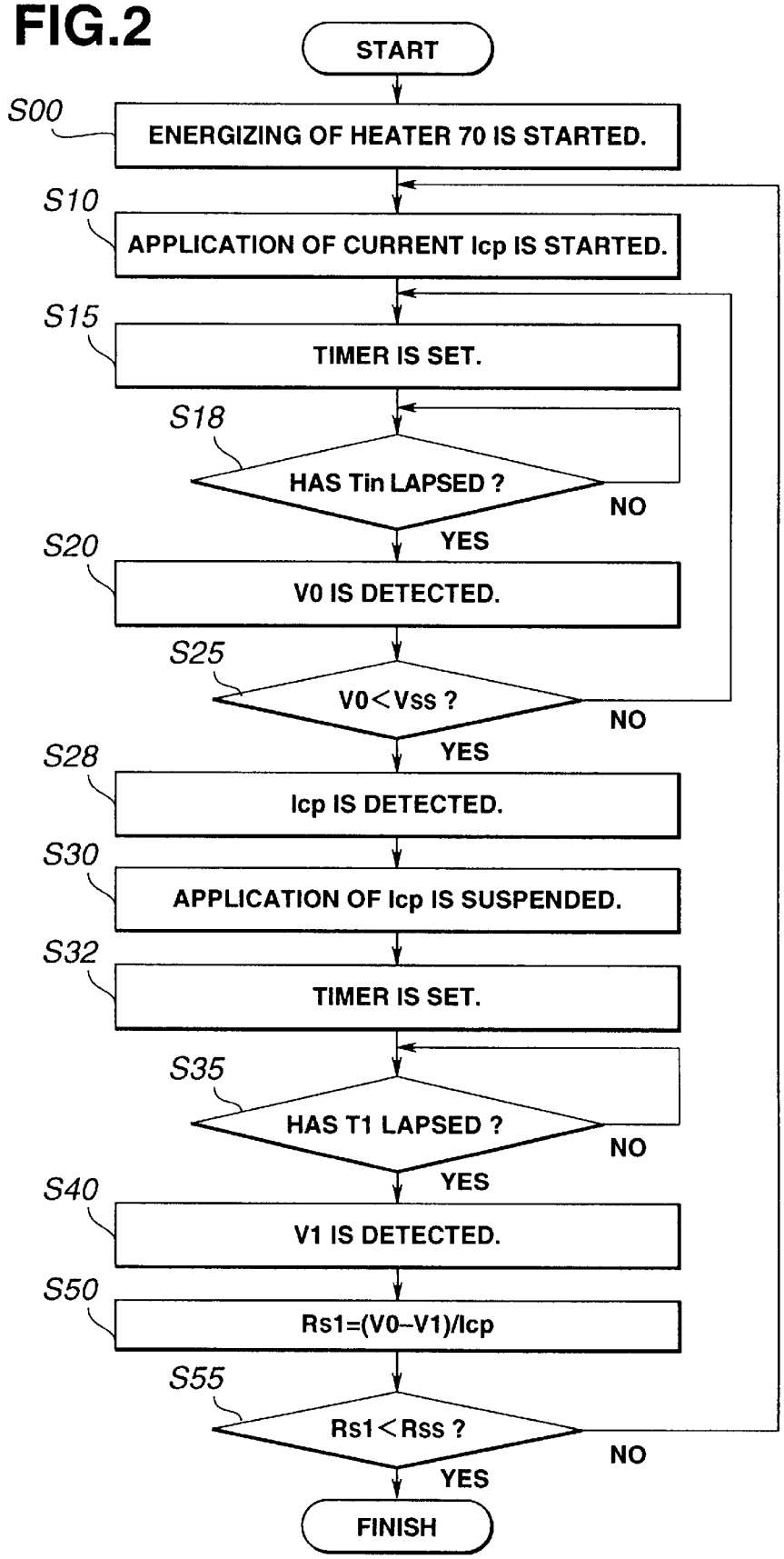
FIG. 2 is a flowchart of a control routine for the controller of FIG. 1.

FIG. 2 is a flowchart of a control routine for the controller 50 for detection of an activated condition according to an embodiment of the present invention. Firstly, immediately after the engine starts, the controller 50 starts application of a current to the heater 70 by way of the heater control circuit 60 (S00). Then, the controller 50 supplies a current Icp for pumping of oxygen to the electromotive force cell 24 (S10). Then, the timer is set (S15) and the lapse of a predetermined time Tin is waited for (S18). After the lapse of time Tin, the voltage across the both electrodes of the electromotive force cell is detected and labeled as V0 (S20). Then, the voltage V0 is compared with a voltage Vss which has previously been determined (S25). The voltage Vss in practical use is preferably within the range of from 1.1 to 2.0 volts and most preferably 1.5 volts. If V0 is smaller than Vss, the current Icp flowing through the electromotive force cell is detected (S28). In this instance, if the current Icp is a previously known value, the value is referred to as Icp, and if not, measurement or calculation of Icp is executed at this stage. In this embodiment, Icp is computed from V0 and several previously known voltages. Then, application of Icp is suspended (S30) and a timer is set (S32). The control is held on standby until the time measured by the timer reaches T1 (S35). In this embodiment, a time of 25 ms is set as T1. At the point of time when time T1 elapses after application of Icp is stopped, the voltage across the electrodes at the opposite faces of the electromotive force cell is detected and labeled as V1 (S40). Then, the resistance Rs1 of the electromotive force cell is computed from V0 and V1 by the following expression (1).

[Expression 1]

$$Rs1=(V0-V1)/Icp$$

Then, the resistance Rs1 is compared with a value Rss which has been prepared previously (S55). When Rs1 is smaller than Rss it is judged that the electromotive force cell has put into an activated condition, i.e., the wide range air-fuel ratio sensor has been put into an activated condition, and the routine for detection of the activated condition is completed and the control proceeds to a normal air-fuel ratio detecting routine. Further, if Rs1 is larger than Rss, it is judged that the electromotive force cell has not yet been put into an activated condition and the control is returned back to the first step to wait for the lapse of time Tin. The value Rss in practical use is preferably within the range of from 1 to 5 KΩ and most preferably 3 kΩ.

Figure 3:
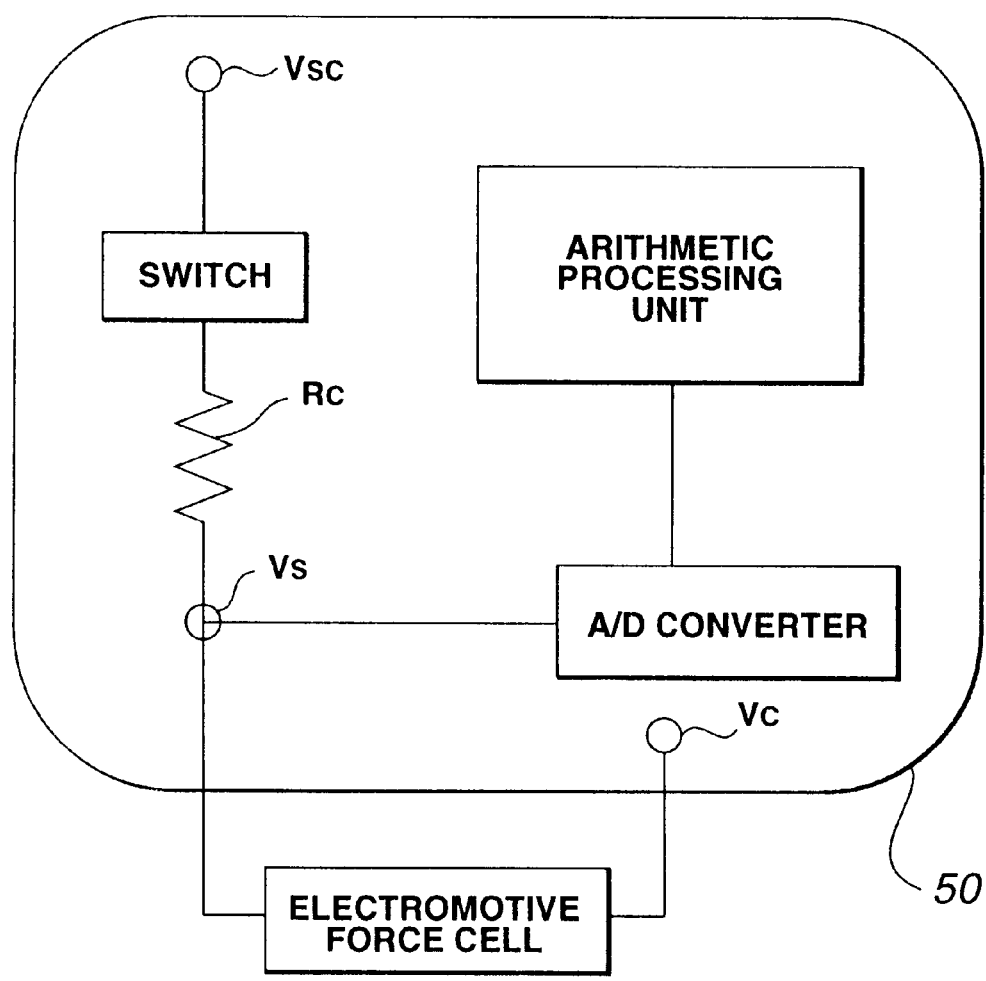
FIG. 3 is a diagram of a circuit for applying or suspending application of Icp to an electromotive force cell.

FIG. 3 shows a circuit for applying Icp to the electromotive force cell or for stopping or suspending application of same. A reference resistor Rc is connected in series to the Vs+ electrode of the electromotive force cell, so that a predetermined voltage Vsc is applied to the electromotive force cell by way of the reference resistor Rc. A predetermined voltage Vc is applied to the Vs– electrode of the electromotive force cell. The voltage (electric potential) Vs+ at the Vs+ electrode of the electromotive force cell is detected from the junction between the Vs+ electrode and the reference resistor Rc by an arithmetic processing unit incorporated in the controller 50 and by using an A/D converter. With this circuit structure, Icp is detected through calculation by using the following expression (2).

[Expression 2]

$$Icp=(Vsc-Vs+)/Rc$$

Further, the voltage Vs across the both electrodes of the electromotive force cell is obtained by calculating the difference between the voltage (electric potential) Vs+ at the Vs+ electrode and the voltage (electric potential) Vs− at the Vs− electrode, but with this circuit structure the voltage Vs− is a fixed voltage Vc so the above described voltages V0 and V1 can be detected by detecting Vs+ at respective measurement timings and subtracting Vc from the detected Vs+.

Figure 4:
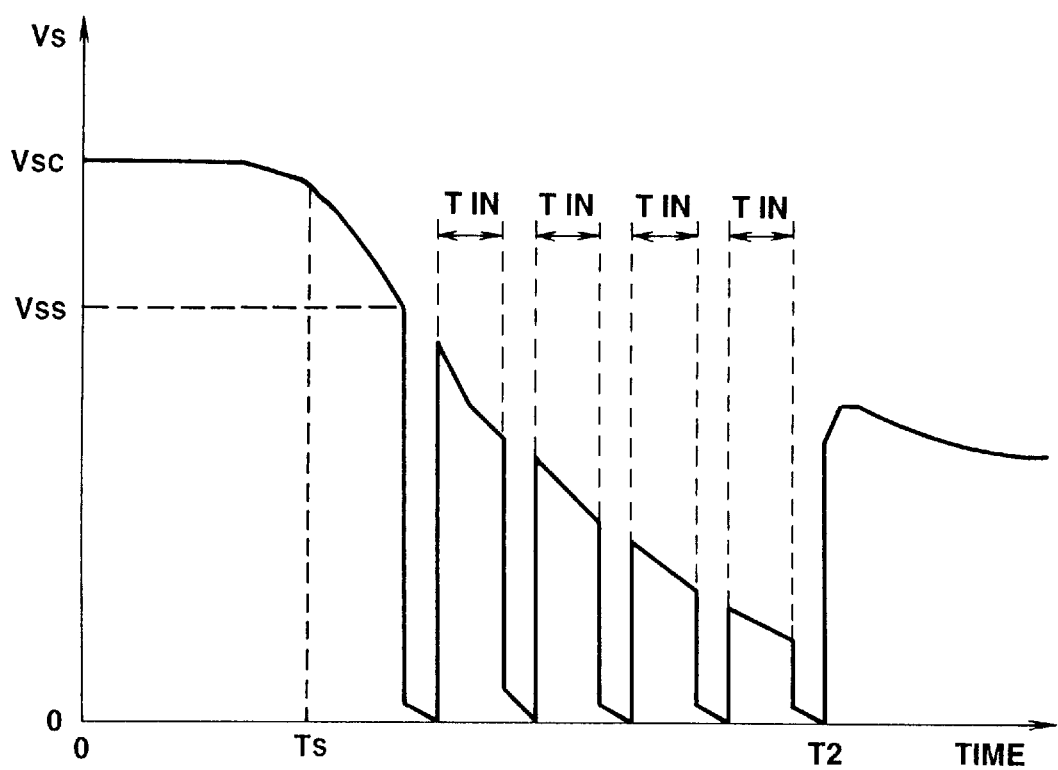
FIG. 4 is a view of a waveform representative of a variation of a voltage Vs across electrodes at opposite side surfaces of an electromotive force cell in relation to a current Icp passed through the electromotive force cell and as a function of a time elapsing after heating of the electromotive force cell starts.

FIG. 4 shows a variation of voltage Vs across the electrodes at the opposite side surfaces of the electromotive force cell in relation to the current Icp passed through the electromotive force cell and a time, in case the detection of an activated condition according to an embodiment of the present invention is executed. Immediately after energizing of the heater starts, the resistance of the electromotive force cell is considerably large as compared with the reference resistance Rc, so the voltage Vs is mostly applied to the electromotive force cell for making Icp flow therethrough. After that, as the electromotive force cell is heated by the heater, its temperature becomes higher, while on the other hand its resistance decreases. Thus, the voltage Vs across the electrodes at the opposite side surfaces of the electromotive force cell decreases gradually, while on the other hand the current Icp flowing through the electromotive force cell increases gradually. When the voltage Vs becomes smaller than Vss, detection of the activated condition of the sensor is started.

The pump cell is not driven before the sensor has been put into an activated condition, so the atmosphere in the gap between the electromotive force cell and the pump cell is not regulated to a theoretical air-fuel ratio. Though it depends on the conditions, the atmosphere is assumed to be in a condition of a lean mode or mixture in this embodiment. Accordingly, an electromotive force generated by the electromotive force cell depending upon the difference of oxygen partial pressure between the gap and the oxygen reference chamber is quite small. For this reason, the voltage Vs across the electrodes at the opposite side surfaces of the electromotive force cell can be mostly considered as a reverse electromotive force cell which is generated by passing Icp through the resistance value Rs of the electromotive force cell.

The process for detection of the activated condition is repeated at a predetermined time interval Tin (specifically, a time interval which is obtained by adding to Tin a time necessary for executing detection of the activated condition).

Figure 5:
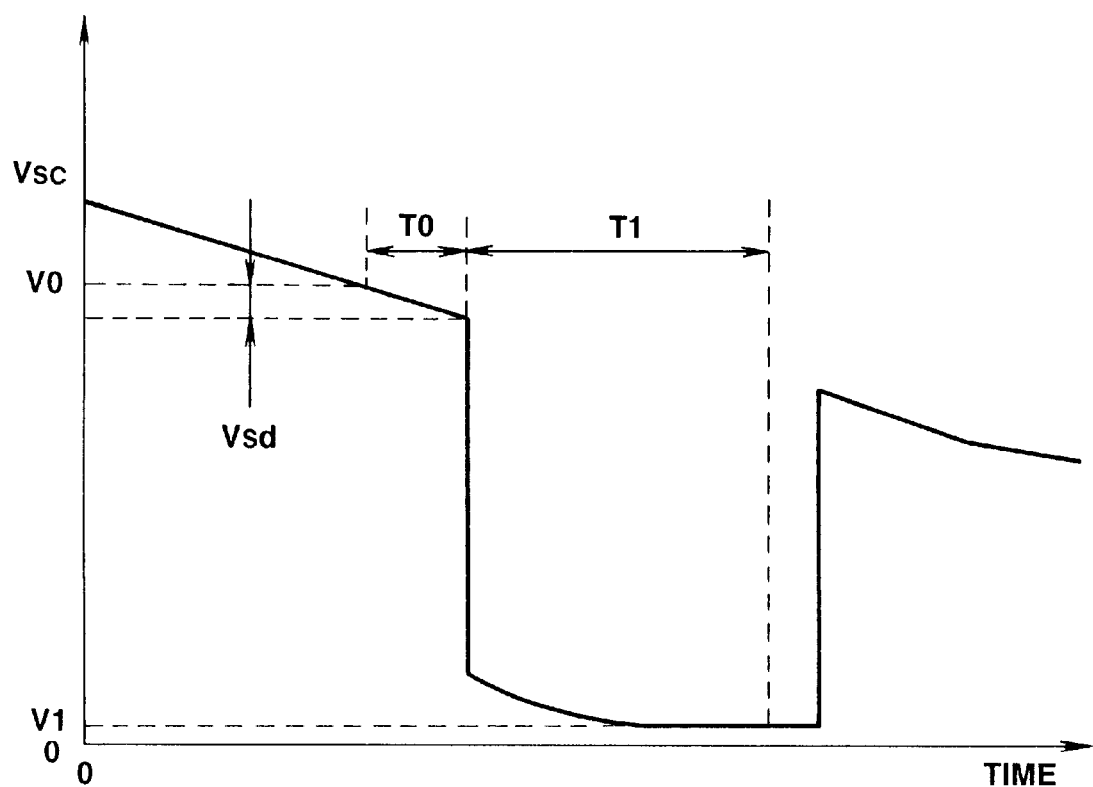
FIG. 5 is an enlarged view of a waveform representative of a variation of the voltage Vs in the process of detecting the activity.

FIG. 5 is a graph of an enlarged variation of the voltage Vs in one activated condition detecting process. The voltage Vs is measured when the time T1 has lapsed after application of the current Icp had been stopped and is labeled as V1. Further, although the voltage V0 is measured immediately before application of the current Icp is started, the period of time T0 elapsing from measurement of V0 till suspension of application of Icp varies depending upon the ability of the controller 50. In this instance, it is desirable that the variation Vsd of the voltage Vs during the time elapsing from measurement of V0 till stoppage of application of Icp is sufficiently small as compared with the difference between V1 and V0.

Figure 6:
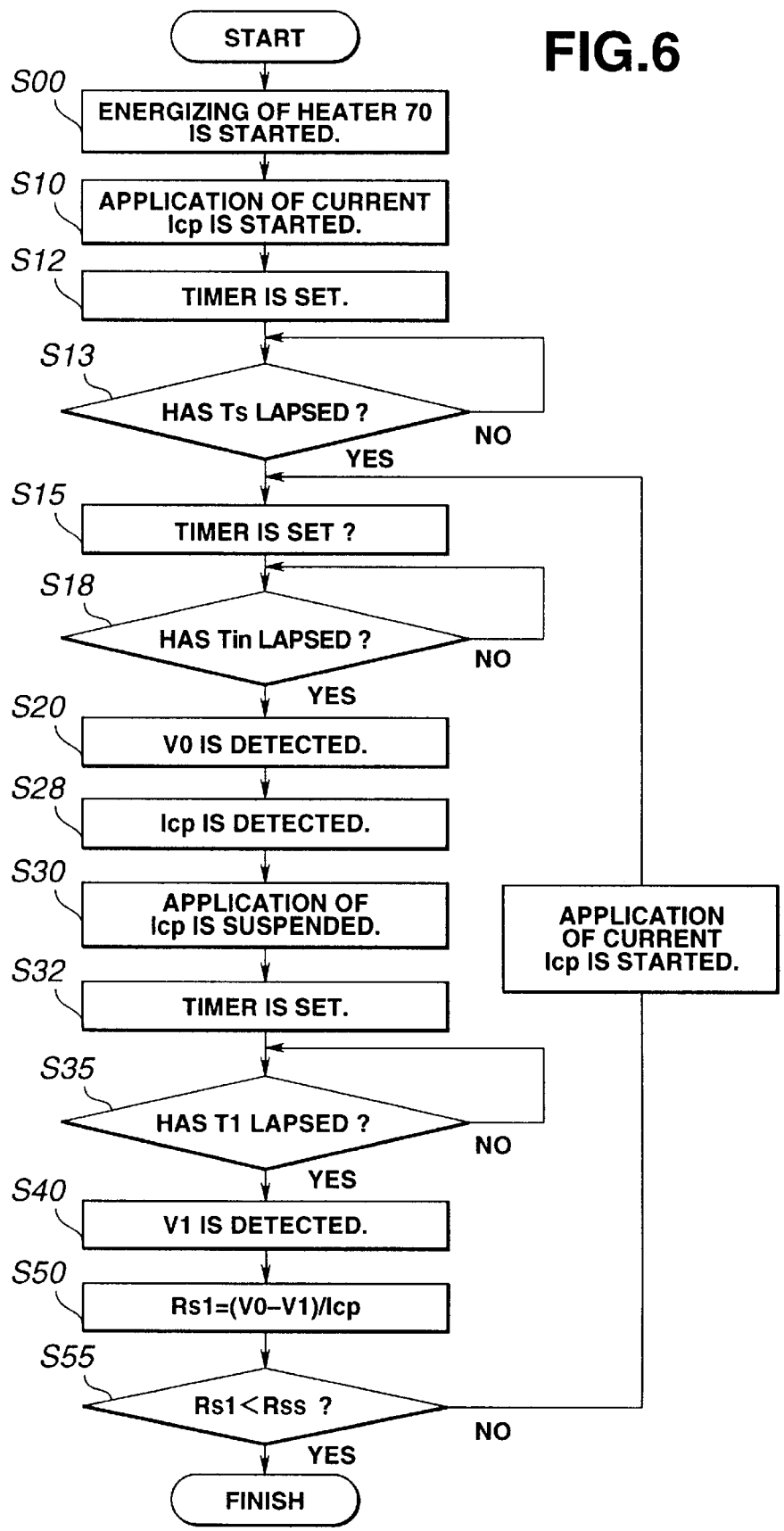
FIG. 6 is a flowchart of a control routine for a method of detecting an activated condition of a wide range air-fuel ratio sensor according to another embodiment of the present invention.
Figure 8A:
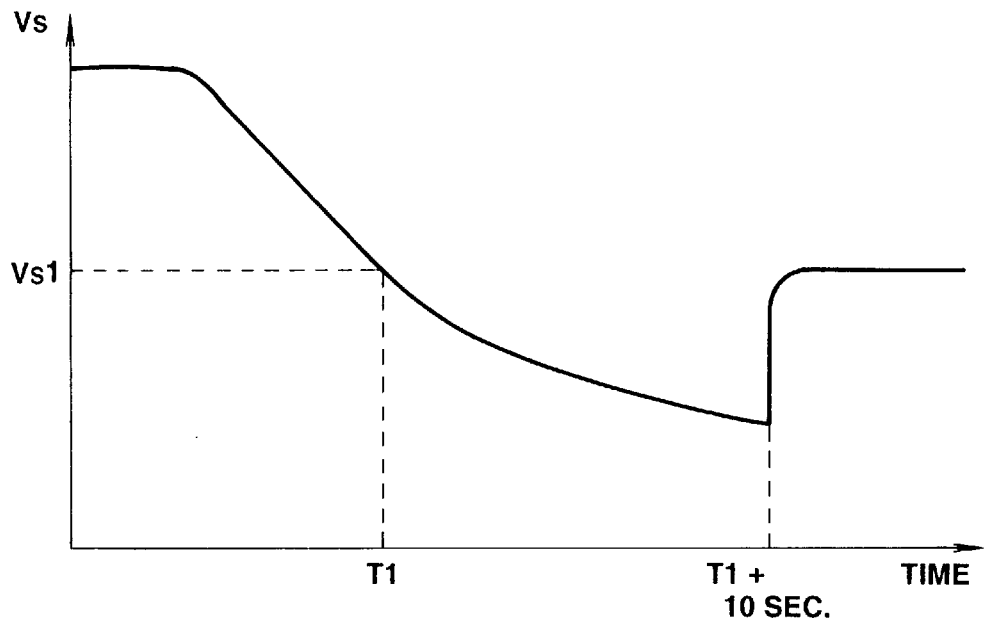
FIG. 8A is a graph of a waveform representative of a voltage of an electromotive force cell according to a prior art technology.
Figure 8B:
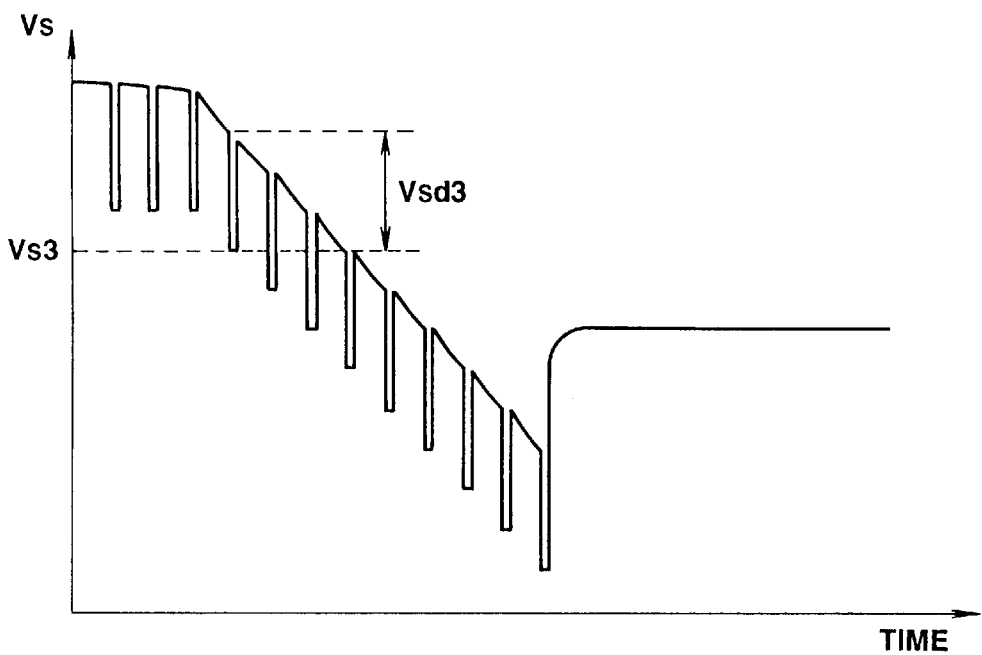
FIG. 8B is a graph of a waveform representative of a voltage of an electromotive force cell according to another prior art technology.

FIG. 6 is a flowchart of a routine for detection of an activated condition according to another embodiment of the present invention. The routine is mostly the same as that of the previous embodiment described with respect to FIG. 2, from the technical point of view but differs from same only in that the timing at which it is started to suspend application of Icp is set at the point of time after lapse of a predetermined time Ts since energizing of the heater is started. More specifically, the step S25 in the previous embodiment for examining the magnitude or value V0 on the basis of which the application of Icp or suspension of same is determined, is deleted and in place therefore new steps S12 and S13 for measuring the time elapsing after energizing of the heater is started are added. In this embodiment, measurement of Vs is not made to start at the same time with starting of the heater, so by setting Ts at the time by which the sensor or electromotive force cell is assumed to be put into an activated condition, it becomes unnecessary to stop or suspend supply of the current Icp several times and repeat detection of the activated condition, thus making it possible to prevent or at least restrain deterioration of the electromotive force cell otherwise resulting from repeated application of pulsed voltage. The time Ts in practical use is preferably within the range of from 5 to 12 seconds and preferably 8 seconds.

EXAMPLE

In the table of FIG. 7, there are shown test results obtained in case air-fuel ratio control of an engine is made by installing an activated condition detecting device having the wide range air-fuel ratio sensor according to the present invention on an exhaust pipe and the time T1 in the first embodiment is varied, i.e., the time T2 from starting of energizing of the heater till detection of the activity of the electromotive force cell, the air-fuel ratio which exists immediately after the activated condition has been detected and the air-fuel ratio control has started and which is measured by another wide range air-fuel ratio sensor which has been put into a sufficiently activated condition, and the durable number of times by which the sensor could be used when subjected to a durability test which repeats start and stop of an engine.

As will be understood from the table of FIG. 7, in case the time T1 is set to be shorter than 10 ms to detect the activated condition of the sensor, the time elapsing from energizing of the heater till detection of the activated condition becomes shorter but the actual air-fuel ratio immediately after the air-fuel ratio control starts is a little below the theoretical air-fuel ratio (i.e., a little leaner). Further, the durable number of times by which the sensor can be used is considerably small. On the other hand, in case T1 is set to be longer than 50 ms to make judgment on the activated condition, a good result is obtained on the durable number of times by which the sensor can be used and on the accuracy of the air-fuel ratio but a fairly long tire is necessitated until the air-fuel ratio control by the sensor is started.

From the above, it is desirable that the time T1 elapsing from suspension of application of Icp to be passed through the electromotive force cell till detection of the voltage Vs is set to be within the range from 10 ms to 50 ms.

From the foregoing, it will be understood that by the activated condition detecting method and apparatus for a wide range air-fuel ratio sensor according to the present invention, it becomes possible to detect the activated condition of the electromotive force cell accurately and therefore the air-fuel ratio of the engine can be detected accurately. Further, even in case the electrode of the electromotive force cell is deteriorated, the entire activated condition inclusive of the deterioration of the electrode can be detected, so the activated condition of the sensor can be detected accurately even if the sensor is deteriorated.

What is claimed is:

1. A method of detecting an activated condition of a wide range air-fuel ratio sensor, wherein the air-fuel ratio sensor includes two cells each having an oxygen ion conductive solid electrolytic body heated by a heater and two porous electrodes disposed on opposite sides of the oxygen ion conductive solid electrolytic body, respectively, the two cells being disposed so as to oppose each other with a gap therebetween, one of the cells serving as a pump cell pumping oxygen out of or into the gap, and the other of the cells serving as an electromotive force cell for generating a voltage according to a difference in oxygen concentration between an oxygen reference chamber and the gap, the method comprising the steps of:

applying a current or voltage to the electromotive force cell;

detecting a voltage V0 across the electrodes at opposite side surfaces of the electromotive force cell;

suspending said step of applying a current or voltage after said voltage V0 becomes equal to or smaller than a predetermined value Vss ranging from 1.1 to 2.0 volts;

detecting a voltage V1 across the electrodes at the opposite side surfaces of the electromotive force cell after a lapse of time ranging from 10 ms to 50 ms after said suspending; and detecting a resistance value Rs1 of the electromotive force cell on the basis of said voltage V0 and said voltage V1 and judging that the wide range air-fuel ratio sensor has been activated when said resistance value Rs1 is equal to or smaller than a predetermined value Rss ranging from 1 to 5 k$\Omega$.

2. A method of detecting an activated condition of a wide range air-fuel ratio sensor, wherein the air-fuel ratio sensor includes two cells each having an oxygen ion conductive solid electrolytic body heated by a heater and two porous electrodes disposed on opposite sides of the oxygen ion conductive solid electrolytic body, respectively, the two cells being disposed so as to oppose each other with a gap therebetween, one of the cells serving as a pump cell for pumping oxygen out of or into the gap, and the other of the cells serving as an electromotive force cell for generating a voltage according to a difference in oxygen concentration between an oxygen reference chamber and the gap, the method comprising the steps of:

applying a current or voltage to the electromotive force cell;

detecting a voltage V0 across the electrodes at opposite side surfaces of the electromotive force cell;

suspending said step of applying a current or voltage after the lapse of a predetermined time Ts ranging from 5 to 12 seconds after the heater starts being energized;

detecting a voltage V1 across the electrodes at the opposite side surfaces of the electromotive force cell after the lapse of time ranging from 10 ms to 50 ms after said suspending; and detecting a resistance value Rs1 of the electromotive force cell on the basis of said voltage V0 and said voltage V1 and judging that the wide range air-fuel ratio sensor has been activated when said resistance value Rs1 is equal to or smaller than a predetermined value Rss ranging from 1 to 5 k$\Omega$.

3. An apparatus for detecting an activated condition of a wide range air-fuel ratio sensor, the air-fuel ratio sensor including two cells each having an oxygen ion conductive solid electrolytic body heated by a heater and two porous electrodes disposed on opposite sides of the oxygen ion conductive solid electrolytic body, respectively, the two cells being disposed so as to oppose each other with a gap therebetween, one of the cells serving as a pump cell for pumping oxygen out of or into the gap, and the other of the cells serving as an electromotive force cell for generating a voltage according to a difference in oxygen concentration between an oxygen reference chamber and the gap, the apparatus comprising:

current or voltage applying means for applying a current or voltage to the electromotive force cell;

V0 voltage detecting means for detecting a voltage V0 across the electrodes at opposite side surfaces of the electromotive force cell;

suspending means for suspending said applying of a current or voltage to the electromotive force cell after said voltage V0 becomes equal to or smaller than a predetermined value Vss ranging from 1.1 to 2.0 volts;

V1 voltage detecting means for detecting a voltage V1 across the electrodes at the opposite side surfaces of the electromotive force cell after a lapse of time ranging from 10 ms to 50 ms after said applying of a current or voltage to the electromotive force cell is suspended; and activity detecting means for detecting a resistance value Rs1 of the electromotive force cell on the basis of said voltage V0 and said voltage V1 and judging that the wide range air-fuel ratio sensor has been activated when said resistance value Rs1 is equal to or smaller than a predetermined value Rss ranging from 1 to 5 k$\Omega$.

4. An apparatus for detecting an activated condition of a wide range air-fuel ratio sensor, the air-fuel ratio sensor including two cells each having an oxygen ion conductive solid electrolytic body heated by a heater and two porous electrodes disposed on opposite sides of the oxygen ion conductive solid electrolytic body, respectively, the two cells being disposed so as to oppose each other with a gap therebetween, one of the cells serving as a pump cell for pumping oxygen out of or into the gap, and the other of the cells serving as an electromotive force cell for generating a voltage according to a difference in oxygen concentration between an oxygen reference chamber and the gap, the apparatus comprising:

current or voltage applying means for applying a current or voltage to the electromotive force cell;

V0 voltage detecting means for detecting a voltage V0 across the electrodes at opposite side surfaces of the electromotive force cell;

suspending means for suspending said applying of a current or voltage after the lapse of a predetermined time Ts ranging from 5 to 12 seconds after the heater starts being energized;

V1 voltage detecting means for detecting a voltage V1 across the electrodes at the opposite side surfaces of the electromotive force cell after a lapse of time ranging from 10 ms to 50 ms after said applying of a current or voltage to the electromotive force cell is suspended; and activity detecting means for detecting a resistance value Rs1 of the electromotive force cell on the basis of said voltage V0 and said voltage V1 and judging that the wide range air-fuel ratio sensor has been activated when said resistance value Rs1 is equal to or smaller than a predetermined value Rss ranging from 1 to 5 k$\Omega$.

* * * * *